United States Patent
Malhotra et al.

(10) Patent No.: US 10,071,062 B2
(45) Date of Patent: Sep. 11, 2018

(54) METHODS FOR THE TREATMENT OF HEPATITIS C

(71) Applicant: Cipla Limited, Mumbai (IN)

(72) Inventors: Geena Malhotra, Mumbai (IN); Kalpana Joshi, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/364,825

(22) Filed: Nov. 30, 2016

(65) Prior Publication Data

US 2017/0157064 A1    Jun. 8, 2017

(30) Foreign Application Priority Data

Dec. 8, 2015  (IN) .......................... 4631/MUM/2015

(51) Int. Cl.
*A61K 31/05* (2006.01)
*A61K 45/06* (2006.01)

(52) U.S. Cl.
CPC .............. *A61K 31/05* (2013.01); *A61K 45/06* (2013.01)

(58) Field of Classification Search
CPC ................................. A61K 31/05; A61K 45/06
USPC ....................................................... 514/734
See application file for complete search history.

(56) References Cited

U.S. PATENT DOCUMENTS

2008/0161324 A1*  7/2008  Johansen ............. A61K 31/135
                                                                514/255.03

OTHER PUBLICATIONS

Hillung, et al., "Characterization of the interaction between hepatitis C virus NS5B and the human oestrogen receptor alpha", Journal of General Virology 93, 2012, 780-785.

Murakami, et al., "Selective estrogen receptor modulators inhibit hepatitis C virus infection at multiple steps of the virus life cycle", Microbes and Infection 15, 2013, 45-55.

Watashi, et al., "Anti-hepatitis C Virus Activity of Tamoxifen Reveals the Functional Association of Estrogen Receptor with Viral RNA Polymerase NS5B", The Journal of Biological Chemistry vol. 282, No. 45, Nov. 9, 2007, 32765-32772.

* cited by examiner

*Primary Examiner* — Yong Liang Chu

(74) *Attorney, Agent, or Firm* — Meunier Carlin & Curfman LLC

(57) ABSTRACT

The present invention relates to method of treatment of hepatitis C using hexestrol or a derivative thereof. The methods of the present invention can be used in patients with hepatitis C administering hexestrol or a derivative thereof in combination with one or more anti-hepatitis C drugs.

7 Claims, 1 Drawing Sheet

_US 10,071,062 B2_

METHODS FOR THE TREATMENT OF HEPATITIS C

CROSS REFERENCE TO RELATED APPLICATION

This application claims the benefit of Indian Application 4631/MUM/2015, filed on Dec. 8, 2015, the contents of which are incorporated herein in its entirety.

FIELD OF THE INVENTION

The present invention relates to method of treating hepatitis C by administering a synthetic, non-steroidal estrogenic compound, alone or optionally in combination with one or more anti-hepatitis C drugs to a subject in need thereof. In particular, the present invention pertains to methods for the treatment of hepatitis C viral infection in humans by administering hexestrol alone or in combination with one or more anti-hepatitis C drugs.

BACKGROUND

Hepatitis C is a largely asymptomatic liver disease caused by the hepatitis C virus (HCV). HCV is an escalating public health problem and burdens an estimated 3% of the world's population. According to the World Health Organization (WHO), approximately 130-150 million individuals worldwide have been infected with HCV, and about 5,00,000 deaths occur due to HCV-related liver diseases each year. The viral disease is transmitted sexually or parenterally by contaminated blood, blood products, and needles or from infected mothers or carrier mothers to their offspring. HCV infected patients, due to the high percentage of individuals inflicted with chronic infections are at an elevated risk of developing cirrhosis of the liver, subsequent hepatocellular carcinoma and terminal liver disease. HCV is the most prevalent cause of hepatocellular cancer and of patients requiring liver transplantations in the western world.

HCV has an RNA genome, as it is an envelope, positive-sense, single-stranded virus. At least six genetic strains of HCV have been identified and studied. Based on a comparison of the deduced amino acid sequence and the extensive similarity in the 5'-untranslated region, HCV has been classified as a separate genus in the _Flaviviridae_ family. All members of the _Flaviviridae_ family have enveloped virions that contain a positive stranded RNA genome encoding all known virus-specific proteins via translation of a single, uninterrupted, open reading frame.

The single strand HCV RNA genome is approximately 9,500 nucleotides in length and has a single open reading frame (ORF) encoding a single large polyprotein of about 3,000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV.

A number of potential molecular targets for drug development of direct-acting antivirals (DAAs) as anti-HCV therapeutics have now been identified including, but not limited to, the NS2-NS3 autoprotease, NS4A protease, the N3 protease, the N3 helicase, and the NS5B polymerase.

HCV infection is currently treated with antiviral medications, e.g. pegylated interferon (Peg-IFN) administered alone or in combination with ribavirin. Combination therapy with pegylated interferon (Peg-IFN) and ribavirin (RBV) is now successful in about half of the cases, but it is currently prohibitively expensive, requires long-term treatment, and is associated with suboptimal efficacy, poorer efficacy among patients with certain genotypes and common severe side-effects that make the treatment intolerable for many patients. In much of the world, such treatments are not economically feasible. New direct-acting antiviral drugs such as protease and polymerase inhibitors, either with or without interferon and/or ribavirin, have the potential to increase the response rate and to decrease the duration of treatment. Challenges facing current treatment of HCV include lack of efficacy in patients with difficult-to-treat disease, such as patients with cirrhosis or infected with HCV genotype 1 (who represent a majority of US HCV infections), the toxicity of combination therapy, and the difficulty of therapy, and the poor reception of these treatments by many patients.

Although attempts have been made in the prior art to develop new treatment options, new therapies for treating HCV-infected patients are desired which selectively inhibit HCV viral replication. It takes a great deal of time and money to develop a new drug from a novel chemical compound, hence, it may be easier to use previously developed drugs that can be used for new applications. Giving due consideration to the diversity of the drugs that are in existence, a way forward could be to determine the activity of the existing drugs to address the need for an alternative treatment for hepatitis C.

An object of the present invention is to provide a method for treating hepatitis C.

Another object of the present invention is to provide a method for treating hepatitis C by administering an estrogen receptor modulator, which is a non-steroidal synthetic estrogen compound.

Another object of the present invention is to provide a method for treating hepatitis C by administering a non-steroidal synthetic estrogen compound which is hexestrol.

Yet another object of the present invention is to provide the use of hexestrol for the treatment of hepatitis C.

Yet another object of the present invention is to provide a pharmaceutical composition comprising hexestrol for the treatment of hepatitis C.

SUMMARY

According to one aspect of the invention, there is provided a method of treating hepatitis C comprising administering an estrogen receptor modulator, which is a non-steroidal synthetic estrogen compound.

According to another aspect of the invention, there is provided a method of alleviating or treating hepatitis C comprising administering a non-steroidal synthetic estrogen compound which is hexestrol.

According to yet another aspect of the present invention, there is provided a method of alleviating or treating hepatitis C by administration of hexestrol in combination with one or more anti-hepatitis C drugs.

According to yet another aspect of the invention, there is provided a pharmaceutical composition comprising hexestrol for the treatment of hepatitis C.

According to another aspect of the present invention, there is provided a pharmaceutical composition comprising hexestrol in combination with one or more anti-hepatitis C drugs.

The details of one or more embodiments are set forth in the descriptions below. Other features, objects, and advantages will be apparent from the description and from the claims.

DETAILED DESCRIPTION

Figure 1:
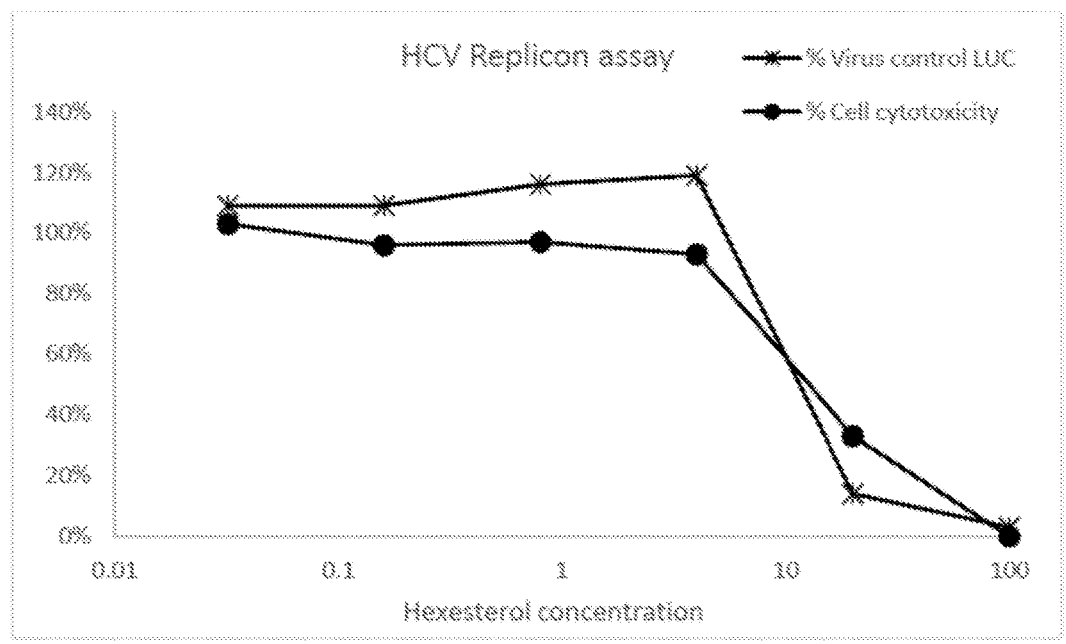
FIG. 1 includes a graph of hexestrol in HCV GT1B replicon assay.
Figure 2:
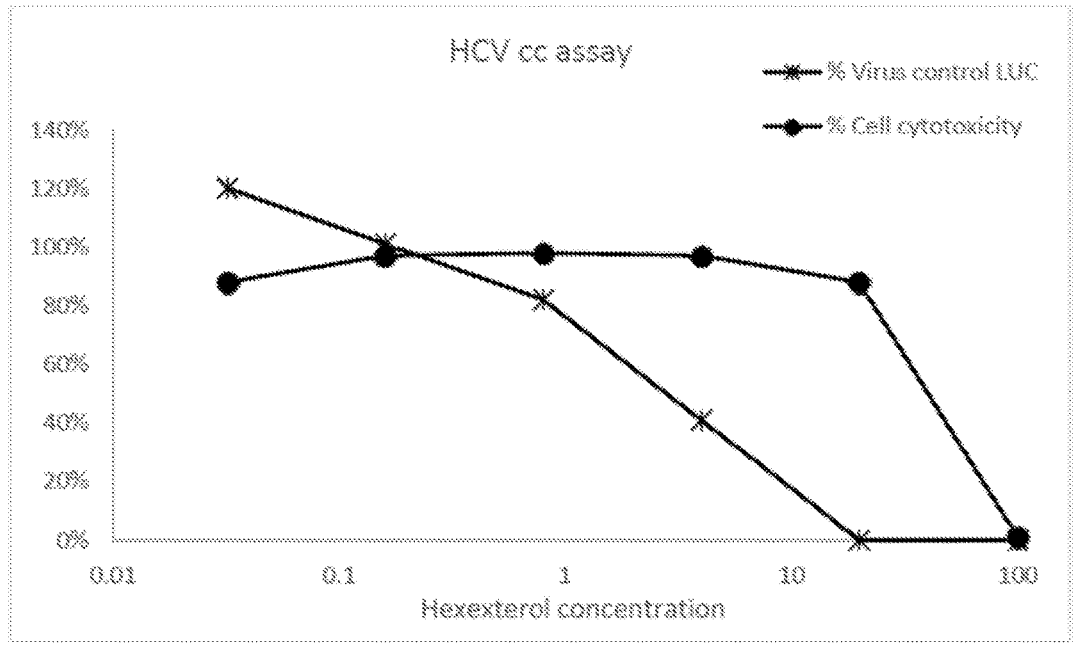
FIG. 2 includes a graph of hexestrol in HCVcc assay

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Hexestrol is a synthetic hydrogenated derivative of diethylstilbestrol (DES). One chemical name for hexestrol is meso 3,4-bis(4-hydroxyphenyl)hexane. Hexestrol has the structural formula:

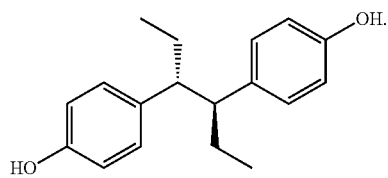 [SMILES: CC[C@H](c1ccc(O)cc1)[C@@H](CC)c1ccc(O)cc1]

The inventors have found that estrogen receptor modulator hexestrol exhibits a significant role in the treatment of hepatitis C. Estrogen receptor (ESR) belongs to the steroid hormone receptor family of the nuclear receptor superfamily. ESR consists of two subtypes, ESRα and ESRβ. As a primary physiological function, ESR is involved in the transcription for downstream genes in response to stimulation by the ligand, estradiol. In the normal state, ESR is mainly located in the cytoplasm and nucleus. The inventors have found that hexestrol exhibited a profound anti-HCV activity possibly through inhibition of multiple steps in the HCV life cycle: entry, viral RNA replication and some post replication step(s), and accordingly blocks viral replication thus indicating potential role in providing a sustained virologic response (SVR—undetectable level of serum HCV RNA maintained for a period of time post-treatment) to a patient infected with hepatitis C. The hepatitis C protein NS5B is responsible for the replication of genetic material through its RNA-dependent RNA polymerase activity. One of the host proteins that interact with NS5B is the estrogen receptor alpha (ESRα). ESRα promoted the participation of NS5B in the HCV Replication Complexes (RC) by escorting NS5B to the HCV RC.

Disclosed herein are methods of treating hepatitis C in a patient in need thereof by administering to the patent an effective amount of hexestrol or derivative thereof. In some embodiments, a hexestrol derivative may be represented by a compound of Formula (1):

(Formula 1)

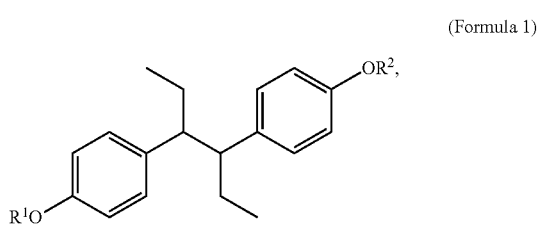

or a pharmaceutically acceptable salt thereof, wherein $R^1$ and $R^2$ are independently selected from hydrogen, C(O)R, C(O)OR, and $PO_3X_2$;

wherein R is independently selected from optionally substituted $C_{1-8}$alkyl, optionally substituted $C_{1-8}$alkaryl, optionally substituted $C_{3-8}$cycloalkyl, optionally substituted $C_{2-12}$heterocyclyl, optionally substituted $C_{2-12}$heteroaryl;

X is independently selected from hydrogen, pharmaceutically acceptable cation, or $R^1$ (as defined above). The compound of Formula (1) may be in the meso configuration, or may be enantioenriched, for instance at least 80%, 85%, 90%, 95%, 97.5% or 99% are in the (R,R) enantiomer, or the (S,S) configuration.

In some embodiments, the optionally substituted $C_{1-8}$alkyl or $C_{1-8}$alkaryl is substituted with an amino group, so as to yield a partial compound of Formula (1a):

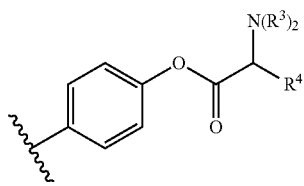

where $R^3$ is independently selected from hydrogen and optionally substituted $C_{1-8}$alkyl, and $R^4$ is selected from hydrogen, optionally substituted $C_{1-6}$alkyl; optionally substituted $C_{3-8}$cycloalkyl, optionally substituted $C_{2-12}$heterocyclyl, optionally substituted $C_{2-12}$heteroaryl. Exemplary substituents for $R^4$ include mercapto, methylmercapto, amino, hydroxyl, COOH, guanidine, $CONH_2$ and the like. In some instances, $R^4$ may together with one or both of $R^3$ form a ring. Such compounds may be obtained by esterifying an appropriate hexestrol compound (e.g., one or both of $R^1$ and $R^2$ being hydrogen) with an amino acid, for instance an α-amino acid.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Preferably, hexestrol or derivative thereof may be administered to the subject once daily, twice daily or thrice daily. A typical recommended daily dosage regimen can range from about 0.1 mg to 1000 mg, preferably from 0.1 mg to 500 mg, more preferably from 1 mg to 100 mg, more preferably from 1 mg to 10 mg. Preferably, hexestrol or derivative thereof may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution and sprinkles, transdermal patches, however, other dosage forms such as controlled release formulations, lyophilized formulations, modified release formulations, delayed release formulations, extended release formulations, pulsatile release formulations, dual release formulations and the like. Liquid and semisolid dosage forms (liquids, suspensions, solutions, dispersions, ointments, creams, emulsions, microemulsions, sprays, patches, spot-on), parenteral, topical, inhalation, buccal, nasal etc. may also be envisaged under the ambit of the invention. The inventors of the present invention have also found that the solubility properties of hexestrol may be improved by nanosizing thus leading to better bioavailability and dose reduction of the drug.

In one embodiment, hexestrol may be present in the form of nanoparticles which have an average particle size of less than 2,000 nm, less than 1,500 nm, less than 1,000 nm, less than 750 nm, less than 500 nm, or less than 250 nm.

Suitable excipients may be used for formulating the dosage form according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

Depending on the pathological stage, patient's age and other physiological parameters, and the extent of invasion, hexestrol or derivative thereof may require specific dosage amounts and specific frequency of administrations. Preferably, hexestrol or derivative thereof may be administered at least once, twice or thrice a day in an amount from 0.1 mg to 100 mg. In some embodiments, hexestrol or derivative thereof may be administered such that the total daily dose is in an amount from 1-100 mg, 5-100 mg, 10-100 mg, 15-100 mg, 20-100 mg, 25-100 mg, 30-100 mg, 35-100 mg, 40-100 mg, 45-100 mg, 50-100 mg, 10-50 mg, 15-50 mg, 20-50 mg, 25-50 mg, 30-50 mg, 35-50 mg, 40-50 mg, 10-25 mg, or 15-25 mg. In certain embodiments, hexestrol or derivative thereof is administered in an amount that the total daily dose is greater than 10 mg. When hexestrol or derivative thereof is administered as a pharmaceutically acceptable salt, the dose levels refer the equivalent amount of hexestrol or derivative thereof free base.

In some embodiments, hexestrol or derivative thereof may be administered to a hepatitis C patient for a period of at least 2 weeks, at least 4 weeks, at least 6 weeks, at least 10 weeks, at least 12 weeks, at least 15 weeks, at least 20 weeks, at least 30 weeks, at least 40 weeks, or at least 52 weeks. In some instances, hexestrol or derivative thereof may be administered for a period of 2-52 weeks, 2-104 weeks, or 2-208 weeks.

Hexestrol or derivative thereof may be used for the treatment of hepatitis C in mammals, especially humans, in monotherapy mode or in a combination therapy (e.g., dual combination, triple combination etc.) mode such as, for example, in combination with one or more anti-hepatitis C drugs. In some instances, the hexestrol or derivative thereof or combination therapy can be administered to patients that are not undergoing estrogen replacement therapy, or in patients diagnosed with a condition for which estrogen replacement therapy is indicated.

There is provided a method of alleviating or treating hepatitis C by administration of hexestrol or derivative thereof optionally in combination with one or more anti-hepatitis C drugs.

Preferably, one or more anti-hepatitis C drugs that may be envisaged under the scope of the present invention may comprise from categories of anti-hepatitis C drugs for the treatment of hepatitis C such as, but not limited to, recombinant Human Interferon Alfa such as pegylated interferon alfa-2a or pegylated interferon alfa-2b (collectively "peginterferon" or "PEG"), nucleoside analogs for example ribavirin, direct acting antivirals (for example daclatasvir, boceprevir and telapravir), NS3/4A protease inhibitors (PIs) (for example simeprevir), nucleotide NS5B polymerase inhibitors (for example sofosbuvir), NS5A Inhibitors (for example daclatasvir), non-nucleoside NS5B Polymerase Inhibitors (for example dasabuvir) or multi-class combination drugs (for example sofosbuvir/velpatasvir, ledipasvir/sofosbuvir, ombitasvir/paritaprevir/ritonavir, ombitasvir/paritaprevir/ritonavir and dasabuvir, elbasvir/grazoprevir, daclatasvir/asunaprevir/beclabuvir). Other possible additional agents include chlorcyclizine, hydroxyzine pamoate, benztropine mesylate, tamoxifen, clomifene, raloxifene, and muscarinic receptor antagonists (atropine, scopolamide, ipratropium, tiotropium, and the like).

The use of hexestrol or derivative thereof may preferably be associated with one or more of the above referenced anti-hepatitis C drugs as a combination therapy (either of the same functional class or other) depending on various factors like drug-drug compatibility, patient compliance and other such factors wherein the said combination therapy may be administered either simultaneously, sequentially, or separately for the treatment of hepatitis C.

Hexestrol or derivative thereof may be provided with one or more anti-hepatitis C drugs in the form of a kit, wherein the kit includes hexestrol or derivative thereof and at least one other anti-hepatitis C drug, and instructions for their administration to a hepatitis C patient.

According to the present invention there is provided a pharmaceutical composition comprising hexestrol or derivative thereof in combination with one or more anti-hepatitis C drugs.

In certain embodiments, the administration of hexestrol or derivative thereof, either alone or in combination with one or more anti-hepatitis drugs, can lower detectable HCV-RNA levels in a hepatitis patient. For instance, methods disclosed herein can lower HCV-RNA levels by at least 10%, at least 20%, at least 30%, at least 40%, at least 50%, at least 60%, at least 70%, at least 80%, at least 90%, or at least 95% relative to HCV-RNA levels prior to initiating treatment. In some instances, hexestrol or derivative thereof can be administered to a patient such no HCV-RNA is detectable in the patient after the treatment course is complete. HCV-RNA levels can be determined by quantitative, multi-cycle reverse transcriptase PCR. Such techniques are known, for instance in U.S. Pat. No. 6,172,046, col. 4, line 50-col. 6, line 5, which is hereby incorporated by reference. As used herein, no detectable HCV-RNA describes a condition in which there are less than 100 copies per ml serum of the patient.

The term "combination" as used herein, defines either a fixed combination in one dosage unit form, a non-fixed combination or a kit containing individual parts for combined administration.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a hepatitis C virus including viral resistance. Within the meaning of the present invention, the term "treat" also includes to arrest, delay the onset (i.e., the period prior to clinical manifestation of a disease) and/or reduce the risk of developing or worsening a disease.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Example 1

HCV Replicon Assay

Stable HCV replicons of different genotypes may be used for anti-HCV evaluation.

The HCV replicon antiviral evaluation assay examined the effects of compounds at six serial dilutions. Human interferon alpha-2b (rIFNα-2b) and/or Sofosbuvir were included in each run as a positive control compound.

Briefly, the replicon cells were plated at 5,000 cells/well into 96-well plates that were dedicated for the analysis of cell numbers (cytotoxicity) or antiviral activity. On the following day, samples were diluted with assay media and added to the appropriate wells. Cells were processed 72 hours later when the cells were still sub-confluent. For the luciferase endpoint assay, HCV replicon levels were assessed as replicon-derived Luc activity. The concentration of drug that reduced cell viability was assessed by the fluorometric CytoTox-1 cell proliferation assay (Promega), (expressed as cell numbers). For the qRT-PCR/TaqMan assay, total RNA was extracted from the replicon cells using RNeasy 96 kit (Qiagen) according to the manufacturer's protocol. Real-time RTPCR/TaqMan assays were performed to measure copy numbers of the replicon RNA and cellular ribosomal RNA. Where applicable $EC_{50}$ (concentration inhibiting HCV replicon by 50%), $EC_{90}$ (concentration inhibiting HCV replicon by 90%), $CC_{50}$ (concentration decreasing cell viability by 50%), $CC_{90}$ (concentration decreasing cell viability by 90%) and SI (selectivity indices: $CC_{50}/EC_{50}$ and $CC_{90}/EC_{90}$) values were derived.

Infectious HCVcc Assay

Huh7.5 cells were grown in Dulbecco's modified essential media (DMEM), 10% fetal bovine serum (FBS), 1% penicillin-streptomycin (pen-strep), 1% Non-essential amino acids (NEAA) in a 5% CO2 incubator at 37° C. Huh7.5 cells were seeded at $1\times10^4$ cells per well into 96-well plates according to Southern Research Institute standard format. Test articles were serially diluted with DMEM plus 5% FBS. The diluted compound in the amount of 50 μl was mixed with equal volume of cell culture-derived HCV (HCVcc), then applied to appropriate wells in the plate. Human interferon alpha-2b (rIFNα-2b) and/or Sofosbuvir were included as a positive control. After 72 hr incubation at 37° C., the cells were lysed for measurement of luciferase activity using *Renilla* Luciferase Assay System (Promega) according to manufacturer's instruction. The number of cells in each well were determined by CytoTox-1 reagent (Promega). Test articles were tested at 6 serial dilutions in triplicate to derive, if applicable, $EC_{50}$ and $EC_{90}$ (concentration inhibiting HCVcc infectivity by 50% and 90%, respectively), $CC_{50}$ (concentration decreasing cell viability by 50%) and SI (selectivity index: $CC_{50}/EC_{50}$) values (Table 1).

| Study | Study Title | Objective of study | $CC_{50}$ | $EC_{50}$ | Hexestrol (Selectivity index) |
|---|---|---|---|---|---|
| In vitro | In vitro HCV replicon assay | Check the efficacy of compounds post infection | 27.4 | 10.9 | 2.51 |
| In vitro | In vitro HCV cc assay | Check the efficacy of compounds pre infection | 50.4 | 2.85 | 14.2 |

Hexestrol showed significant anti-Hepatitis C activity when tested in Hepatitis C viral infectivity and HCV replicon assays as illustrated above.

Example 3

Dosage Forms

Dosage Form A—Representative Hexestrol Tablets

| Ingredients | Qty/Tab (mg) |
|---|---|
| Hexestrol | 0.2-5 |
| Microcrystalline cellulose | 10-25 |
| Lactose Monohydrate | 20-80 |
| Croscarmellose Sodium | 5-10 |
| Povidone | 3-10 |
| Colloidal anhydrous silica | 1-5 |
| Magnesium Stearate | 1-5 |

Process:
1) Hexestrol and lactose monohydrate were sifted and blended.
2) Croscarmellose sodium, Povidone, and colloidal anhydrous silica were sifted and blended with above material of step 1.
3) Sifted Magnesium stearate was added to the above material of step 2 and blended.
4) The final blend was compressed into tablets.

Dosage Form B—Representative Hexestrol Tablets

| Ingredients | Quantity Mg/tablet |
|---|---|
| Hexestrol | 0.5-20 |
| Lactose monohydrate | 10-50 |
| Hypromellose (HPMC K4M/K15 M/K100 M) | 20-60 |
| Microcrystalline cellulose | 5-20 |
| Colloidal silicon dioxide | 1-5 |
| Magnesium stearate | 2-8 |

Process:
1. Hexestrol and lactose monohydrate were sifted and blended.
2. Hypromellose was dissolved in sufficient quantity of purified water.
3. Step no 1 material was granulated using Hypromellose solution.
4. The wet mass obtained in step 3 was loaded in suitable equipment for drying and dried.
5. Colloidal silicon dioxide and Microcrystalline cellulose were sifted and blended along with the dried granules of step 4.
6. Sifted Magnesium stearate was added to the above material of step 5 and blended.
7. The final blend was compressed into tablets.

Dosage Form C—Hexestrol Tablets

| Ingredients | Quantity mg/tablet |
|---|---|
| Hexestrol | 20-200 |
| Pre-gelatinized starch | 30-150 |
| Spray-dried lactose (Flow lac 100) | 20-100 |
| Croscarmellose sodium | 15-45 |
| Magnesium stearate | 5-20 |
| Opadry ready mix | 2.5-10 |
| Purified water | 3-10 |

Process:
1. Hexestrol, pre-gelatinized starch, Spray-dried lactose and croscarmellose sodium were sifted and blended.
2. Sifted magnesium stearate was added and the blend was lubricated.
3. The lubricated blend was then compressed into tablets.
4. Opadry ready mix was dissolved in sufficient quantity of purified water to prepare the film coating solution.
5. The tablets were film-coated using the coating solution of step 4.

Dosage Form D—Hexestrol Tablets

| Ingredients | Qty (mg/tab) |
|---|---|
| Hexestrol | 25-300 |
| Microcrystalline cellulose | 100-300 |
| Povidone | 4-16 |
| Starch | 10-45 |
| Colloidal silicon dioxide (Aerosil) | 1-6 |
| Talc | 3-12 |
| Magnesium Stearate | 3-12 |

Process:
1. Hexestrol, Microcrystalline cellulose, povidone, and starch were sifted and blended.
2. Colloidal silicon dioxide and Talc were added and blended.
3. Sifted Magnesium stearate was added and blended.
4. The lubricated blend was compressed into tablets.

Dosage Form E—Hexestrol Injection

| Ingredients | Qty per unit |
| --- | --- |
| Hexestrol | 25-300 mg |
| Ethyl alcohol | 10-20% |
| Benzyl alcohol | 10-20% |
| Polysorbate 80 | 0.1-1.0% |
| α-tocopherol | 0.01-0.1% |
| Castor oil (super refined) | q.s. 2-5 mL |

Process:
1. Benzyl alcohol and ethyl alcohol were added and mixed.
2. Hexestrol was added and dissolved into the above solution.
3. Polysorbate 80 and α-tocopherol were added to the above solution obtained in step 2 and mixed.
4. Castor oil was added and mixed.
5. The above solution was filtered, filled in suitable container and sealed.

Dosage Form F—Hexestrol Injection

| Ingredients | Qty per unit |
| --- | --- |
| Hexestrol | 25-300 mg |
| Benzyl alcohol | 2-10% |
| Sesame oil | Q.s. 2-5 mL |

Process:
1. Sesame oil and Benzyl alcohol were added and mixed.
2. Hexestrol was added and dissolved into the above solution.
3. The above solution was filtered, filled in suitable container and sealed.

Dosage Form G—Hexestrol Soft Gelatin Capsules

| Ingredients | Qty per unit |
| --- | --- |
| Hexestrol | 25-300 |
| D-alpha-tocopheryl polyethylene glycol 1000 succinate (TPGS) | 50-400 |
| Polyethylene glycol 400 | 200-350 |

Process:
1. D-alpha-tocopheryl polyethylene glycol 1000 succinate (TPGS) was heated to 50° C. until liquefied.
2. Approx. 80% of Polyethylene glycol was added and mixed until homogenous solution was obtained.
3. Hexesterol was added and dissolved in solution obtained in step 2.
4. Remaining quantity of polyethylene glycol was added to the solution of step 3 and cooled to room temperature.
5. The final solution was then filled in soft gelatin capsules.
6. The capsule shells were the dried until the desired moisture levels and packed in a suitable container.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of treating hepatitis C infection in human patient comprising administering a pharmaceutical composition comprising hexestrol or derivative thereof, or a pharmaceutically acceptable salt thereof to a patient in need thereof, wherein the hexestrol or derivative thereof, or pharmaceutically acceptable salt thereof is the only anti-hepatitis C agent in the composition.

2. The method of claim 1, wherein hexestrol or derivative thereof is administered daily in a dose from 1 mg to 100 mg per day.

3. The method of claim 1, further comprising administering at least one other anti-hepatitis C drug to the patient.

4. The method of claim 1, wherein the composition comprises hexestrol or derivative thereof in an amount from 1-100 mg.

5. The method of claim 1, wherein the composition comprises at least one other anti-hepatitis C drug.

6. The method of claim 4, wherein the composition comprises hexestrol or derivative thereof in an amount from 1-10 mg.

7. The method of claim 1, wherein the composition comprises hexestrol.

* * * * *